United States Patent
Imura et al.

(10) Patent No.: US 9,174,897 B2
(45) Date of Patent: Nov. 3, 2015

(54) METHOD FOR PURIFYING TRANS-1,3,3,3-TETRAFLUOROPROPENE

(71) Applicant: Central Glass Company, Limited, Ube-shi, Yamaguchi (JP)

(72) Inventors: Hideaki Imura, Saitama (JP); Naoto Takada, Saitama (JP); Masamune Okamoto, Fujimino (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 13/929,261

(22) Filed: Jun. 27, 2013

(65) Prior Publication Data
US 2014/0051896 A1    Feb. 20, 2014

(30) Foreign Application Priority Data

Jun. 28, 2012 (JP) .................. 2012-145381
Jun. 25, 2013 (JP) .................. 2013-133058

(51) Int. Cl.
*C07C 17/389* (2006.01)
*C07C 17/38* (2006.01)
*C07C 21/18* (2006.01)
*C07C 19/08* (2006.01)
(Continued)

(52) U.S. Cl.
CPC .............. *C07C 17/389* (2013.01); *C07C 21/18* (2013.01); *C07B 2200/09* (2013.01); *C07C 17/38* (2013.01); *C07C 19/08* (2013.01); *C07C 19/10* (2013.01); *C07C 21/22* (2013.01)

(58) Field of Classification Search
CPC ...... C07C 19/08; C07C 21/18; C07C 17/389; C07C 17/38
USPC .......................................... 570/179, 177, 262
See application file for complete search history.

(56) References Cited

U.S. PATENT DOCUMENTS

| | | | |
|---|---|---|---|
| 5,302,187 A * | 4/1994 | Itoh et al. ................... | 95/11 |
| 6,548,719 B1 | 4/2003 | Nair et al. | |
| 7,597,744 B2 | 10/2009 | Thomas et al. | |
| 7,829,747 B2 | 11/2010 | Wang et al. | |

(Continued)

FOREIGN PATENT DOCUMENTS

| | | |
|---|---|---|
| EP | 1 231 195 A1 | 8/2002 |
| JP | 2000-229894 A | 8/2000 |

(Continued)

OTHER PUBLICATIONS

"UOP Molecular Sieves ype 13-X", Mar. 21, 2015, Scott Specialty Gas (Two (2) pages).

*Primary Examiner* — Jafar Parsa
*Assistant Examiner* — Medhanit Bahta
(74) *Attorney, Agent, or Firm* — Crowell & Morning LLP

(57) ABSTRACT

Disclosed is a method for purifying a trans-1,3,3,3-tetrafluoropropene, in which a composition containing trans-1,3,3,3-tetrafluoropropene and at least one impurity selected from the group consisting of $C_2H_3ClF_2$, $CF_3CH_2CHClF$, $CF_3CH_2CHF_2$, $CHF_2CH{=}CF_2$, $CF_3CH{=}CHCl$, $CF_3CH{=}CH_2$, $CF_3C{\equiv}CH$, and cis-1,3,3,3-tetrafluoropropene is brought into contact with a solid adsorbent to reduce an impurity content thereof. By this method, it is possible to remove the impurity in trans-1,3,3,3-tetrafluoropropene by a simple operation.

9 Claims, 1 Drawing Sheet

(51) Int. Cl.
*C07C 19/10* (2006.01)
*C07C 21/22* (2006.01)

(56) References Cited

U.S. PATENT DOCUMENTS

| | | | |
|---|---|---|---|
| 7,829,748 B1 * | 11/2010 | Tung et al. | 570/164 |
| 8,802,870 B2 | 8/2014 | Gonzalez et al. | |
| 2009/0253820 A1 | 10/2009 | Bowman et al. | |
| 2009/0270661 A1 | 10/2009 | Wang et al. | |
| 2010/0162738 A1 | 7/2010 | Low et al. | |
| 2011/0052652 A1 | 3/2011 | Suzuki et al. | |
| 2011/0172470 A1 | 7/2011 | Hamasaki et al. | |
| 2011/0270001 A1 | 11/2011 | Ishihara et al. | |
| 2012/0266750 A1 * | 10/2012 | Thomas et al. | 95/131 |
| 2013/0065044 A1 | 3/2013 | Bowman et al. | |

FOREIGN PATENT DOCUMENTS

| | | |
|---|---|---|
| JP | 2002-047218 A | 2/2002 |
| JP | 3271005 B2 | 4/2002 |
| JP | 2005-504097 A | 2/2005 |
| JP | 3869184 B2 | 1/2007 |
| JP | 2008-19243 A | 1/2008 |
| JP | 2009-514902 A | 4/2009 |
| JP | 2009-263365 A | 11/2009 |
| JP | 2009-539598 A | 11/2009 |
| JP | 2010-64990 A | 3/2010 |
| JP | 2010-100613 A | 5/2010 |
| JP | 2010-202640 A | 9/2010 |
| JP | 2011-504538 A | 2/2011 |
| WO | WO 01/36355 A1 | 5/2001 |
| WO | WO 2011045559 A1 * | 4/2011 |

* cited by examiner

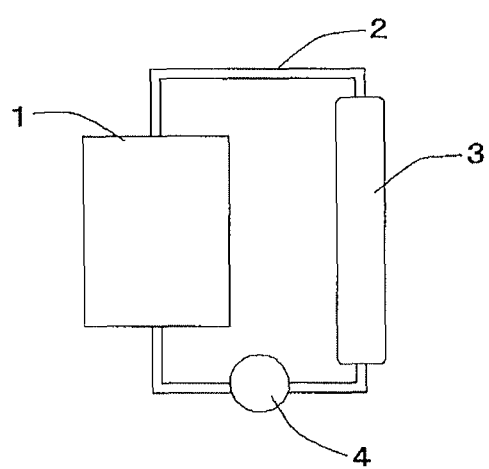

METHOD FOR PURIFYING TRANS-1,3,3,3-TETRAFLUOROPROPENE

TECHNICAL FIELD

The present invention relates to a method for purifying trans-1,3,3,3-tetrafluoropropene, which is useful for refrigerants, working fluids, foaming agents, intermediates for medicines and agrochemicals, electronic materials, fluorine-containing resin materials, etc., and a method for producing trans-1,3,3,3-tetrafluoropropene using the same.

BACKGROUND OF THE INVENTION

Since 1,3,3,3-tetrafluoropropene contains a double bond in the molecule, it decomposes rapidly in the atmosphere and is an environment-adaptive fluorocarbon having no concern for the effect on the ozone layer depletion, the global warming, etc. Furthermore, 1,3,3,3-tetrafluoropropene is a fluorine-containing olefin, and there exist cis-trans isomers. In the following, using the identification number and the additional sign, trans-form may be referred to as 1234zeE, and cis-form as 1234zeZ. In the case of no distinction between trans-form and cis-form, or of a mixture of them, it may be referred to as 1234ze.

As methods for producing 1,3,3,3-tetrafluoropropene (1234ze), the methods described in Patent Publication 1 to Patent Publication 3 can be mentioned.

Patent Publication 1 discloses a method for producing 1,3,3-tetrafluoropropene (1234ze) by reacting 1,1,1,3,3-pentafluoropropane (in the following, may be referred to as 245fa) with a potassium hydroxide aqueous solution in the presence of a crown ether.

In a method for producing 1,3,3,3-tetrafluoropropene (1234ze) by subjecting 1,1,1,3,3-pentafluoropropane (245fa) to a dehydrofluorination reaction in a gas phase in the presence of a catalyst, Patent Publication 2 discloses a method for producing 1,3,3,3-tetrafluoropropene (1234ze) by using a zirconium compound-supported catalyst prepared by supporting a zirconium compound on a metal oxide or an activated carbon.

Patent Publication 3 discloses a method for producing 1234ze, comprising the step of reacting 1,1,1,3,3-pentachloropropane (in the following, may be referred to as 240) with hydrogen fluoride to obtain 1-chloro-3,3,3-trifluoropropene (in the following, may be referred to as 1233zd) and the step of reacting the obtained 1233zd with hydrogen fluoride in a gas phase in the presence of a fluorination catalyst to obtain 1,3,3,3-tetrafluoropropene (1234ze). In the above-mentioned 1-chloro-3,3,3-trifluoropropene (1233zd), there exist cis-trans isomers. In the following, trans-form may be referred to as 1233zdE, and cis-form as 1233zdZ. In the case of no distinction between trans-form and cis-form, or of a mixture of them, it may be referred to as 1233zd.

Furthermore, in the field of refrigerants, working fluids, foaming agents, intermediates for medicines and agrochemicals, or electronic materials, in the case of using trans-1,3,3-tetrafluoropropene (1234zeE), it is preferable that 1234zeE has a high purity without containing impurities. In uses for refrigerants, working fluids, and foaming agents, particularly in the case of using as a refrigerant for car air conditioners, 1234zeE of high purity is preferred.

In particular, it is not preferable to have contamination of 1234zeE by CFCs (chlorofluorocarbons), HCFCs (hydrochlorofluorocarbons) or HFCs (hydrofluorocarbons), as impurities, which are saturated compounds. In these compounds, there are ones that are stable in the atmosphere and cause the ozone layer depletion or global warming and ones that show toxicity. Therefore, in case that 1234zeE contains these compounds as impurities, it has been a problem of necessity to remove them.

The impurities to contaminate 1234zeE can be exemplified by 142 ($C_2H_3ClF_2$ (presumed structure: $CF_2HCH_2Cl$)), 244fa ($CF_3CH_2CHClF$), and 245fa ($CF_3CH_2CHF_2$), which are saturated compounds. They can be exemplified by 1234zc ($CHF_2CH=CF_2$), 1243zf ($CF_3CH=CH_2$), $CF_3C\equiv CH$, 1233zd ($CF_3CH=CHCl$) or cis-1,3,3,3-tetrafluoropropene (1234zeZ, cis $CF_3CH=CHF$), which are unsaturated compounds. In the following, these compounds may be referred to by their identification numbers.

A solid adsorbent, such as zeolite or alumina, is capable of increasing purity of fluorinated hydrocarbons or fluorinated unsaturated hydrocarbons by an adsorptive reduction of hydrogen fluoride, alcohols, etc. contained in the fluorinated saturated hydrocarbons or the fluorinated unsaturated hydrocarbons. Patent Publication 4 discloses a method of an adsorptive reduction of hydrogen fluoride, which is contained in fluorinated hydrocarbons and fluorinated unsaturated hydrocarbons, by such solid adsorbent. Patent Publication 5 discloses a method of an adsorptive reduction of alcohols. Patent Publication 6 discloses a method for drying a fluid comprising a fluoropropene, which method comprises the step of contacting the fluid with a desiccant comprising a molecular sieve having openings which have a size across their largest dimension of from 3 angstroms to 5 angstroms.

As in the methods described in Patent Publications 4-6, it is publicly known to selectively adsorb only small molecules, such as hydrogen fluoride or alcohols, into micropores of zeolite. There is, however, not known a method of conducting a selective adsorptive removal of impurities that have molecular structures and sizes similar to those of the target product.

PRIOR ART PUBLICATIONS

Patent Publications

Patent Publication 1: Japanese Patent Application Publication 2005-504097
Patent Publication 2: Japanese Patent Application Publication 2008-19243
Patent Publication 3: Japanese Patent Application Publication 2010-100613
Patent Publication 4: Japanese Patent Application Publication 2002-047218
Patent Publication 5: Japanese Patent Application Publication 2000-229894
Patent Publication 6: Japanese Patent Application Publication 2009-514902

SUMMARY OF THE INVENTION

The present invention provides a purification method to obtain trans-1,3,3,3-tetrafluoropropene (1234zeE) of high purity.

That is, it is a task to efficiently remove, from a trans-1,3,3,3-tetrafluoropropene (1234zeE) of low purity containing, as impurities in 1234zeE, the above-mentioned 142 ($C_2H_3ClF_2$), 244fa ($CF_3CH_2CHClF$), 245fa ($CF_3CH_2CHF_2$), 1234zc ($CHF_2CH=CF_2$), 1243zf ($CF_3CH=CH_2$), $CF_3C\equiv CH$, 1233zd ($CF_3CH=CHCl$) or cis-1,3,3,3-tetrafluoropropene (1234zeZ, cis $CF_3CH=CHF$), these impurities.

In view of the above-mentioned task, as a result of an eager study, the present inventors have found that, if the trans-1,3, 3,3-tetrafluoropropene (1234zeE) containing the above-mentioned impurities is brought into contact with a solid adsorbent, although these impurities have structures and sizes similar to those of 1234zeE, unexpectedly these impurities can efficiently be reduced. We have found that, in particular, of solid adsorbents, silica-alumina series compounds of high polarities effectively adsorb them, zeolites more effectively adsorb them, and particularly zeolites A and zeolites X specifically adsorb them, thereby completing the present invention.

The present invention includes Inventions 1-5.

[Invention 1]

A method for purifying a trans-1,3,3,3-tetrafluoropropene, comprising the step of bringing a composition containing trans-1,3,3,3-tetrafluoropropene and at least one impurity selected from the group consisting of $C_2H_3ClF_2$, $CF_3CH_2CHClF$, $CF_3CH_2CHF_2$, $CHF_2CH=CF_2$, $CF_3CH=CHCl$, $CF_3CH=CH_2$, $CF_3C\equiv CH$, and cis-1,3,3,3-tetrafluoropropene into contact with a solid adsorbent to reduce an impurity content thereof.

[Invention 2]

The purification method according to claim 1, wherein one of the impurities is cis-1,3,3,3-tetrafluoropropene or $CF_3CH_2CHF_2$.

[Invention 3]

The purification method according to Invention 1 or Invention 2, wherein the solid adsorbent is zeolite A or zeolite X.

[Invention 4]

A method for producing trans-1,3,3,3-tetrafluoropropene, comprising the step of purifying a trans-1,3,3,3-tetrafluoropropene by bringing a composition containing trans-1,3,3,3-tetrafluoropropene and at least one impurity selected from the group consisting of $C_2H_3ClF_2$, $CF_3CH_2CHClF$, $CF_3CH_2CHF_2$, $CHF_2CH=CF_2$, $CF_3CH=CHCl$, $CF_3CH=CH_2$, $CF_3C\equiv CH$, and cis-1,3,3,3-tetrafluoropropene into contact with a solid adsorbent to reduce an impurity content thereof.

[Invention 5]

A solid-liquid, heterogeneous mixture, comprising:
a composition containing trans-1,3,3,3-tetrafluoropropene and at least one organic matter selected from the group consisting of $C_2H_3ClF_2$, $CF_3CH_2CHClF$, $CF_3CH_2CHF_2$, $CHF_2CH=CF_2$, $CF_3CH=CHCl$, $CF_3CH=CH_2$, $CF_3C\equiv CH$, and cis-1,3,3,3-tetrafluoropropene, and
a solid adsorbent.

ADVANTAGEOUS EFFECT OF THE INVENTION

According to the purification method and the production method of the present invention, it is possible to reduce impurities in a trans-1,3,3,3-tetrafluoropropene (1234zeE) by a simple operation to achieve high purification.

BRIEF DESCRIPTION OF THE DRAWINGS

FIGURE is a schematic view of one embodiment of a circulation mode.

DETAILED DESCRIPTION

In the purification method of the present invention, reducing the content of impurities in a trans-1,3,3,3-tetrafluoropropene (1234zeE) refers to reducing the content of at least one impurity selected from the group consisting of 142 ($C_2H_3ClF_2$), 244fa ($CF_3CH_2CHClF$), 245fa ($CF_3CH_2CHF_2$), 1234zc ($CHF_2CH=CF_2$), 1233zd ($CF_3CH=CHCl$), 1243zf ($CF_3CH=CH_2$), $CF_3C\equiv CH$, or cis-1,3,3,3-tetrafluoropropene (1234zeZ, cis $CF_3CH=CHF$) to 50% or lower, preferably 10% or lower, by a contact with a solid adsorbent.

[Method for Purifying trans-1,3,3,3-tetrafluoropropene (1234zeE)]

In the purification method of the present invention, a composition containing at least one selected from the group consisting of 142, 244fa, 245fa, 1243zf, 1234zc, 1233zd, and 1234zeZ, which are impurities, in trans-1,3,3,3-tetrafluoropropene (1234zeE) may be referred to as a crude 1234zeE. The crude 1234zeE may be a composition obtained by any situation. Although the composition ratios are not particularly limited, it is preferable that 1234zeE is a major component, that is, amounts to 50 mass % or greater.

The crude 1234zeE may a reaction product obtained by the step of reacting 1,1,1,3,3-pentachloropropane (240fa) with hydrogen fluoride, or a reaction product obtained by an isomerization of trans-1,3,3,3-tetrafluoropropene (1234zeE), or a reaction product obtained by a dehydrofluorination of 1,1,1,3,3-pentafluoropropane (245fa).

The crude 1234zeE may be one prepared by purifying the above-mentioned reaction mixture by a publicly known method. The purification method can be exemplified by washing with water or liquid, drying, an ordinary distillation or extractive distillation, etc.

In the purification method of the present invention, it is also possible to purify a used trans-1,3,3,3-tetrafluoropropene (crude 1234zeE) containing any of the above-mentioned impurities, which has been recovered after using trans-1,3,3,3-tetrafluoropropene (1234zeE) in the use of solvent, detergent, flux, refrigerant, heat medium, working fluid, or foaming agent, etc.

Normally, in these crude 1234zeE's, the composition of trans-1,3,3,3-tetrafluoropropene (1234zeE) amounts to from 80 mass % to 99.9999 mass %, and the total of the impurities and other impurities amounts to from 0.0001 mass % to 20 mass %. It is preferable if the total amount of the impurities is as less as possible. Normally, it is preferable from 0.0001 mass % to 10 mass %.

Furthermore, it is also possible to apply the purification method of the present invention to crude 1234zeE's prepared by adding the impurities or other components by request from a person skilled in the art. In this case, it is preferable that the concentration of trans-1,3,3,3-tetrafluoropropene (1234zeE) is 90 mass % or greater, and that the total amount of the impurities is 10 mass % or less.

The content of each organic matter contained in the crude 1234zeE is not particularly limited. For example, even if trans-1,3,3,3-tetrafluoropropene (1234zeE) is about 20 mass % and the total amount of the impurities is about 0.1 mass %, it can be applied to the purification method of the present invention as long as a solvent or high-boiling-point component, which is separable by distillation, amounts to the remaining 79.9 mass %. It is possible to obtain trans-1,3,3,3-tetrafluoropropene (1234zeE) of high purity by conducting a distillation operation after reducing the impurities by a solid adsorbent. Prior to conducting the purification method of the present invention, it is preferable to remove water contained in the composition by using a drying agent. As the drying agent, it is possible to mention zeolite 3A or zeolite 4A.

By a computational chemistry technique using a generic function B3LYP//6-31G*, the molecular weight as an index of the molecular size and the molecular surface area or molecular volume in the space-filling model of 1234zeE and the above-mentioned impurities were calculated. With this, correlations between these calculated values and the actual adsorption characteristics were not found.

Dipole moment of 1234zeE was found to be specifically small (1.29 debye) by determining dipole moments of 1234zeE and the impurities using the above-mentioned computational chemistry technique. With this, it is believed that the solid adsorbent selectively adsorbs the impurities having large dipole moments, unlike that an adsorbent selectively adsorbs small-size molecules as described in Patent Publications 4-6. It is believed that the purification of 1234zeE having a specifically small dipole moment has become possible by such characteristic of the solid adsorbent.

TABLE 1

| Rational Formula | Compound Name | Dipole Moment (debye) | Mw | Molecular Surface Area ($Å^2$) | Molecular Volume ($Å^3$) |
|---|---|---|---|---|---|
| E-$CF_3CH=CHF$ | 1234zeE | 1.29 | 114.04 | 108.68 | 84.07 |
| E-$CF_3CH=CHCl$ | 1233zdE | 1.42 | 130.50 | 118.57 | 92.97 |
| $CF_3CH_2CHF_2$ | 245fa | 2.13 | 134.05 | 118.56 | 92.83 |
| HF | HF | 2.17 | 20.01 | 32.33 | 16.77 |
| $CHF_2CH=CF_2$ | 1234zc | 2.25 | 114.04 | 108.69 | 84.24 |
| $H_2O$ | $H_2O$ | 2.39 | 18.02 | 36.43 | 19.39 |
| $CF_3CH=CH2$ | TFP | 3.08 | 96.05 | 103.04 | 79.50 |
| $CF_3C\equiv CH$ | TFPY | 3.17 | 94.04 | 99.95 | 76.33 |
| Z-$CF_3CH=CHF$ | 1234zeZ | 3.79 | 114.04 | 108.08 | 84.06 |

Dipole moment is determined by calculating the electron distribution in the molecule by computational chemistry technique. The electron distribution is determined by solving Schrödinger's wave equation, but it is not possible at the current technological level to solve the wave equation without a hypothesis. Accordingly, the calculated result becomes different depending on the hypothesis. Therefore, when comparing dipole moments, the comparison should be made by the values calculated by the same technique. Although there are various computational chemistry techniques, it is preferable to use a dipole moment determined by particularly density functional theory (DFT) having a good balance between CPU cost (the calculation speed) and reliability of the results. In particular, it is preferable to refer to dipole moment determined by B3LYP//6-31G* or a calculation having a precision more than that.

[Solid Adsorbent]

As the solid adsorbent used in the purification method of the present invention, alumina, silica, silica-alumina, zeolite, clay, activated carbon, or complexes or mixtures of these are preferable. Depending on the desire of a person skilled in the art, it is possible to use a combination of these.

Regarding the alumina, it is possible to use amorphous alumina, crystalline alumina, alumina hydrate, etc. Of these, an alumina low in crystallinity is preferable. For example, it can be exemplified by a trade name of N612N made by Nikki Chemicals Co., which is on the market for catalyst use.

Regarding the silica, it is possible to use amorphous silica, crystalline silica or silica hydrate, etc. Specifically, it is exemplified by silica gel. As commercial products, it is possible to mention, for example, trade names of CARiACT and Q-15 made by Fuji Davison Co.

The silica-alumina series solid adsorbent is exemplified by zeolite and clay (e.g., allophane).

As the zeolite, it is possible to use either a zeolite defined by International Zeolite Association or a zeolite defined by International Mineralogical Association. According to International Zeolite Association, zeolite is defined as being a compound having a composition of ABn (n≈2) forming an open three-dimensional network, wherein A has four bonds and B has two bonds, and as being a substance having a framework density of 20.5 or less.

According to International Mineralogical Association, zeolite is defined as being one satisfying conditions that it is a crystalline substance characterized by a framework structure in which tetrahedrons having four oxygen atoms coordinated to a cation are connected, that the structure has micropores formed of channels and holes and open to the outside, that is, having a size to allow passage of guest molecules, that the channels and the holes are normally occupied by molecules and exchangeable cations, and that continuation of the framework may become discontinuous by OH group or F group occupying one of oxygen atoms of tetrahedron apexes.

As the solid adsorbent suitable for the present invention, it is preferable to use a zeolite recorded in the database by International Zeolite Association. Specifically, it is possible to use one having a structure such as faujasite series, chabazite series, or mordenite series. Faujasite series zeolite can be exemplified by natural zeolite, such as faujasite, and synthetic zeolites such as zeolite A's such as 3A, 4A and 5A, zeolite X's such as 10X and 13X, and Y's. It is also possible to use a combination of these zeolites. Chabazite series zeolite can be exemplified by natural zeolites, such as chabazite, gmelinite, erionite and levynite, and synthetic zeolites such as R, S or T. Mordenite zeolite can be exemplified by mordenite, clinoptilolite, etc. of natural or synthetic products.

In the case of zeolite, it is possible to use either a natural product or an artificially synthesized product, but an artificially synthesized product having a stable quality is preferable.

As the activated carbon, it is possible to use an activated carbon of vegetable series, lime series, and petroleum series. In particular, vegetable series activated carbons using wood, charcoal and coconut husk coal as the raw materials, and lime activated carbons using bituminous coal, lignite etc. as the raw materials are preferably used. In the case of activated carbon, polarity is low by its single use. Therefore, it is preferable to use that together with silica, alumina or silica-alumina or in the form of a composite material by doping with these.

Of these solid adsorbents, an artificially synthesized zeolite, of which artificially synthesized product with a stable quality is industrially available, is particularly preferable. Zeolite A or X, which is called Molecular Sieves (TM, it is the same in the following), is superior in availability. K (potassium)-substituted zeolite A (referred to as MS-3A, KA or Molecular Sieves 3A), Na (sodium)-substituted zeolite A (referred to as MS-4A, NaA or Molecular Sieves 4A), Ca (calcium)-substituted zeolite A (referred to as MS-5A, CaA or Molecular Sieves 5A), Ca (calcium)-substituted zeolite X (referred to as MS-10X, CaX or Molecular Sieves 10X), and Na-substituted zeolite X (referred to as MS-13X, NaX or Molecular Sieves 13X) are good. In particular, 10X and 13X, which are zeolites X with substituted potassium ions or sodium ions, are preferable solid adsorbents.

Furthermore, in the purification method of the present invention, irrespective of whether it is a natural zeolite or a synthetic zeolite, it is also possible to use a zeolite modified by baking, acid contact, base contact or ion exchange, etc. The ion suitable for the ion exchange is an ion of alkali metals or an ion of alkali earth metals. The ion of alkali metals can be exemplified by, for example, lithium ion, sodium ion, potassium ion, rubidium ion, or cesium ion. The ion of alkali earth metals can be exemplified by, for example, beryllium ion, magnesium ion, calcium ion, strontium ion, or barium ion.

In the synthetic zeolite, according to the desire of a person skilled in the art, it is also possible to change the micropore distribution, the Si/Al ratio, and the contents of other metals.

[Adsorption]

Depending on the type of solid adsorbents, some of them contain or adsorb chlorine atoms. When 1,3,3,3-tetrafluoropropene (1234ze) is brought into contact with this to reduce its impurity content, 1-chloro-3,3,3-trifluoropropene (1233zd) may be generated. When contacting with the solid adsorbent, the crude 1234zeE may be gas or liquid. In the case of gas, 1233zd may be generated notably.

A means for suppressing the generation of 1-chloro-3,3,3-trifluoropropene (1233zd) is to remove chlorine atoms by previously washing zeolite.

As the washing method, there is effective a treatment of immersing zeolite in an ion-exchanged water containing no chlorine ions or pure water, drying after the contact washing, etc. In particular, it is more effective to use an aqueous solution having a concentration of from 0.1 mass % to 5 mass % of an alkali metal fluoride, such as KF, NaF and CsF, etc. In particular, it is effective in the case of having a desire to obtain trans-1,3,3,3-tetrafluoropropene (1234zeE) of a higher purity. 1-chloro-3,3,3-trifluoropropene (1233zd) also, however, contains a double bond and therefore is a substance substantially having no concern to cause the global warming and the ozone layer depletion. Thus, if it is allowed to contain 1233zd, it is possible to omit the above-mentioned washing of zeolite.

It is admissible to use a zeolite in any shape, such as powder, granule or granulated product, as the solid adsorbent of impurities, which is used in the purification method of the present invention. In the case of using in a packed column, a spherical or rod-shaped one is preferable due to its easy handling. The method of contact between the crude 1234zeE and the solid adsorbent is not particularly limited. It can be exemplified by a batch manner in which the solid adsorbent is added to the crude 1234zeE in a container to have a contact for a predetermined time to reduce the content of its impurities, a flow manner in which the crude 1234zeE is allowed to flow through a facility (in the following, it may be referred to as an adsorption column) packed with the solid adsorbent, etc. In the contact in the flow manner, it is also possible to circulate the crude 1234zeE. In the case of packing a column with the adsorbent and making the crude 1234zeE flow, it is preferable to use a solid adsorbent formed to have a shape of beads or pellets, which causes a small loss of pressure. As a method of circulating the crude 1234zeE, for example, as shown in FIGURE, it is possible to use a method in which the liquid of the crude 1234zeE in a tank 1 filled with the crude 1234zeE is allowed to flow through an adsorption column 3 packed with the solid adsorbent by a line 2 and is circulated by a liquid delivery pump 4, and like methods.

In the purification method of the present invention, when the crude 1234zeE is brought into contact with the solid adsorbent to reduce its impurity content, the crude 1234zeE may be either gas or liquid. It is preferable to reduce its impurity content by the contact in the form of liquid, since the amount of treatment of adsorbing the impurities is greater, and the productivity is better.

The time necessary for the adsorption operation of the impurities in the batch manner is normally from 5 minutes to 48 hours, preferably from 30 minutes to 6 hours, more preferably from 60 minutes to 3 hours, although it depends on the abundance ratio of trans-1,3,3,3-tetrafluoropropene (1234zeE) and the solid adsorbent, the temperature upon adsorbing, the initial concentration of impurities, the target concentration after the adsorption, the type and the shape of the adsorbent, etc. In case that the operation time is short, the concentration of the impurities may not lower sufficiently. In general, there is a tendency that the concentration of the impurities lowers abruptly at the initial stage of the adsorption operation and then lowers gradually. Therefore, it is not necessary to spend an excessively long time. Upon this, the abundance ratio of trans-1,3,3,3-tetrafluoropropene (1234zeE) to the solid adsorbent, 1234zeE/the solid adsorbent, by mass is preferably from 1 to 30, although it depends on the temperature upon adsorbing, the initial concentration of impurities, the target concentration after the adsorption, the type and the shape of the adsorbent, etc.

The temperature at the time of the adsorption operation is not particularly limited. It is preferably from $-50°$ C. to $30°$ C., particularly preferably from $-30°$ C. to $10°$ C. If it is higher than $30°$ C., the pressure may become high since 1234zeE has a boiling point of $-19°$ C. For cooling at a temperature lower than $-50°$ C., a special cooling apparatus is necessary, thereby increasing the equipment cost and the operation cost. Therefore, it is economically preferable. It is not necessary to conduct cooling at a temperature lower than $-50°$ C.

The pressure at the time of adsorption is not particularly limited either in batch manner or flow manner. An operation at around ordinary pressure is easy, but according to need it is also possible to conduct a compression by using a pump or a pressurization by adding nitrogen. In particular, in order to make the crude 1234zeE flow into the adsorption column, it is an industrially usual measure to pressure-feed the crude 1234zeE in the form of liquid by using a pump. It is preferable to be used in the purification method of the present invention. In the case of pressure-feeding, pressurization can be conducted at an arbitrary pressure. If pressurization is conducted at an excessively high pressure, a high-price pressure-proof apparatus becomes necessary. Therefore, it is preferable that the pressure is from $-0.05$ MPa to $+1.0$ MPa.

In the case of flow manner, the adsorption condition depends on the number of the flows, the type and the condition of the solid adsorbent, the amount of the solid adsorbent used for packing, the dimensions (inner diameter and length) of the adsorbent column, the adsorption temperature, and the flow rate. It is preferable that the adsorption column has a length/inner diameter ratio of from 3 to 200, preferably from 4 to 50. If the length/inner diameter ratio is small, the removal of the impurities adsorbed by the solid adsorbent may be insufficient. In case that the length/inner diameter ratio is extremely large, the pressure loss becomes large. For example, in case that the number of flows is one, it is preferable that retention time of the crude 1234zeE in the adsorption column is from 1 minute to 120 minutes. Furthermore, linear velocity (void column linear velocity) of the crude 1234zeE in the form of liquid is from 1 cm/hr to 10 m/hr, preferably from 2 cm/hr to 5 m/hr. If the linear velocity is slower than 1 cm/hr, the impurity adsorption treatment time becomes long to lower the efficiency. Therefore, it is not preferable. If it exceeds 10 m/hr, the removal of impurities may be insufficient.

When the solid adsorbent is in a fresh condition prior to use, both of the amount adsorbable and the adsorption rate are large. In a condition after adsorption of a lot of impurities, they become low. In this case, it is possible to regenerate the solid adsorbent by a method called a desorption operation. Specifically, it is possible to regenerate the solid adsorbent by removing the liquid in the adsorption column and then decompression. Upon this, it is acceptable to conduct heating after decompression of the adsorption column. Although it is optional to conduct heating after decompression, the temperature in the case of heating is preferably from 30° C. to 300° C. By conducting a cooling collection of the gas component generated at the time of the desorption treatment, it is possible to obtain a concentrate of the impurities adsorbed by the solid adsorbent.

[Solid-Liquid, Heterogeneous Composition]

Depending on the desire of a person skilled in the art, it is also possible to introduce the solid adsorbent into a container for storing and transporting the crude 1234zeE, thereby storing and transporting them as a solid-liquid, heterogeneous mixture of the crude 1234zeE and the solid adsorbent.

The solid-liquid, heterogeneous mixture in the present invention is a solid-liquid, heterogeneous mixture containing a composition containing at least one organic matter selected from the group consisting of $C_2H_3ClF_2$ (142), $CF_3CH_2CHClF$ (244fa), $CF_3CH_2CHF_2$ (245fa), $CHF_2CH=CF_2$ (1234zc), $CF_3CH=CHCl$ (1233zd), $CF_3CH=CH_2$ (1243zf), $CF_3C\equiv CH$ and cis-1,3,3,3-tetrafluoropropene (1234zeZ) and trans-1,3,3,3-tetrafluoropropene (1234zeE), and the solid adsorbent.

For example, in the present invention, in the case of storing, transporting or selling the crude 1234zeE by using a stainless steel container, it becomes possible by adding the solid adsorbent into the container to provide trans-1,3,3,3-tetrafluoropropene (1234zeE), in which impurities, such as $C_2H_3ClF_2$ (142), $CF_3CH_2CHClF$ (244fa), $CF_3CH_2CHF_2$ (245fa), $CHF_2CH=CF_2$ (1234zc), $CF_3CH=CHCl$ (1233zd), $CF_3CH=CH_2$ (1243zf), $CF_3C\equiv CH$ or cis-1,3,3,3-tetrafluoropropene (1234zeZ), etc., have been reduced.

Upon this, the mass ratio of the crude 1234zeE to the solid adsorbent may suitably be examined, since it depends on embodiments and bulk density of the solid adsorbent. The mass ratio of the crude 1234zeE/the solid adsorbent is preferably from 0.1 to 200, more preferably from 1 to 100. The mass ratio of the crude 1234zeE/the solid adsorbent is preferably from 5 to 50, more preferably from 8 to 40. If the mass ratio is less than 0.1, not only the solid adsorbent becomes excessively necessary, but also the amount of trans-1,3,3,3-tetrafluoropropene (1234zeE) usable for packing the container becomes small. Therefore, it is not preferable. If the mass ratio is greater than 200, a sufficient adsorption effect may not be obtained.

In the case of storing and transporting the above-mentioned solid-liquid, heterogeneous mixture in a container, an environment of low temperature and low humidity is desirable. Specifically, it is from −50° C. to 25° C., preferably from −20° C. to 5° C. In the case being higher than 25° C., trans-1,3,3,3-tetrafluoropropene (1234zeE) may alter depending on the length of the storing period. It is not economical to maintain a temperature lower than −50° C. In the case of high humidity, there are concerns that a metal container corrodes by humidity and that water enters the container when opening and closing the container. Therefore, it is not preferable.

In the above-mentioned flow manner too, it is also possible to conduct a high purification of the crude 1234zeE by stopping the flow, having the crude 1234zeE stay in the adsorption column, storing as the above-mentioned solid-liquid, heterogeneous mixture, and adsorbing the impurities in the solid adsorbent. In this case, although the abundance ratio of the crude 1234zeE to the solid adsorbent is not particularly limited, the mass ratio of the crude 1234zeE/the solid adsorbent is preferably from 0.1 to 3.

EXAMPLES

In the following, the trans-1,3,3,3-tetrafluoropropene (1234zeE) purification method of the present invention is explained in more detail by specifically showing examples, but embodiments of the purification method of the present invention are not limited to this. As to the composition proportions of trans-1,3,3,3-tetrafluoropropene (1234zeE) and the above-mentioned impurities, unless otherwise noted, the areal % measured and recorded by gas chromatography using an FID detector was expressed as %.

Zeolites 1-7 used as the solid catalysts are enumerated in the following. Commercial products were used as Zeolites 1-5, and ones subjected to activation treatments of Zeolite 2 were used as Zeolites 6 and 7. Molecular Sieves and Zeolum are trademarks.

[Zeolite 1]
Ca-A type zeolite (In the following, it may be referred to as CaA.)
made by Wako Pure Chemical Industries, Ltd., trade name: Molecular Sieves 5A pellets (1/16)

[Zeolite 2]
Na—X type zeolite (In the following, it may be referred to as NaX)
made by Wako Pure Chemical Industries, Ltd., Molecular Sieves 13X pellets (1/16)

[Zeolite 3]
Li—X type zeolite, low silica and high alumina (In the following, it may be referred to as LiX.)
made by Tosoh Corporation, Zeolum NSA700 pellets (1.5 mm φ)

[Zeolite 4]
Ca—X Zeolite (In the following, it may be referred to as CaX.)
made by Tosoh Corporation, Zeolum SA600A pellets (1.5 mm φ)

[Zeolite 5]
Na—X type zeolite (In the following, it may be referred to as NaX.)
made by Tosoh Corporation, Zeolum F9 pellets (14-34 mesh (about 1 mm))

[Zeolite 6]
NaX—NaF Aqueous Solution Treatment
A sodium fluoride aqueous solution was prepared by dissolving 15.2 g of sodium fluoride in 3784.8 g of ion exchanged water. After adding 20 g of Zeolite 2 to the sodium fluoride aqueous solution, it was allowed to stand still under room temperature (about 20° C.) for one hour. The zeolite was separated from the aqueous solution by filtration, followed by washing for 4 hours by continuing to pour 4000 g of ion exchanged water on the zeolite while circulating the ion exchanged water. After the washing, the zeolite was maintained at 200° C. and dried by spending 24 hours in an oven. After cooling, heating was conducted for 3 minutes by using a microwave oven at an output power of 600 W, followed by storing in a desiccator with silica gel.

[Zeolite 7]
NaX-Ion Exchange Water Treatment

After adding 20 g of Zeolite 2 to 4000 g of ion exchanged water, it was allowed to stand still under room temperature for one day. The zeolite was separated by filtration, followed by washing for 4 hours by continuing to pour ion exchanged water (4000 g) on the zeolite while circulating the ion exchanged water. After the washing, the zeolite was maintained at 200° C. and dried by spending 24 hours in an oven. After cooling, heating was conducted for 3 minutes by using a microwave oven at an output power of 600 W, followed by storing in a desiccator with silica gel.

Example 1

(An Example in which Zeolite 1 CaA was Used as the Solid Adsorbent)

There were prepared a stainless steel container A (an adsorption experiment container) equipped with a stop valve and having an inner capacity of 50 cc and a container B (a crude 1234zeE feeding container). 6 g of Zeolite 1 was fed into the container A, followed by decompression by a vacuum pump, closing the valve, and immersion in a dry ice/acetone bath for cooling.

Then, the container B charged with 30 g of the crude 1234zeE was cooled by liquid nitrogen to freeze the crude 1234zeE, followed by decompression by using a vacuum pump and then closing the valve.

The container B was immersed and allowed to stand still in a thermostatic bath controlled at 20° C. One hour later, the gas phase portion was analyzed by gas chromatography to determine composition of the crude 1234zeE prior to the adsorption treatment by Zeolite 1.

Then, the container B was taken out of the thermostatic bath. The container B at an upper side was connected to the above-mentioned container A at a lower side. After removing the air of the container A and a connecting portion by using a vacuum pump, a ball valve of the connecting portion was opened. Then, the total amount of the crude 1234zeE of the container B was transferred to the container A to have a contact between the crude 1234zeE and Zeolite 1. After closing the ball valve, the stainless steel container A was taken out of the dry ice/acetone bath and was allowed to stand still in a thermostatic bath of 20° C. 3 hours later, a gas phase portion of the container A was analyzed by gas chromatography to check the impurity adsorption effect by Zeolite 1. The results are shown in Table 2.

It was found by a contact with Zeolite 1 that $CF_3C \equiv CH$ can be reduced from 8 ppm to 4 ppm and that 1243zf can be reduced from 11 ppm to 4 ppm (In Table 1, 0.0000 represents "not detected").

Example 2

(An Example in which Zeolite 2 NaX was Used as the Solid Adsorbent)

There was conducted an adsorptive removal of impurities of the crude 1234zeE by the same procedure as that of Example 1, except in that Zeolite 2 (NaX) was used in place of Zeolite 1 (CaA). The results are shown in Table 2. As a result of bringing Zeolite 2 (NaX) into contact with the crude 1234zeE, the effect of strikingly reducing 1243zf, 245fa and 1234zeZ was found. Furthermore, not only other impurities were also reduced to the detection lower limit, but also trans-1,3,3,3-tetrafluoropropene (1234zeE) was highly purified from 99.8674% to 99.9924%.

Example 3

(An Example in which Zeolite 3 LiX was Used as the Solid Adsorbent)

There was conducted an adsorptive removal of impurities in the crude 1234zeE by the same procedure as that of Example 1, except in that Zeolite 3 (LiX) was used as the solid adsorbent. The results are shown in Table 2. Similarly, impurities were removed, and purity of trans-1,3,3,3-tetrafluoropropene (1234zeE) was increased.

Example 4

(An Example in which Zeolite 4 CaX was Used as the Solid Adsorbent)

There was conducted an adsorptive removal of impurities in the crude 1234zeE by the same procedure as that of Example 1, except in that Zeolite 4 (CaX) was used as the solid adsorbent. The results are shown in Table 2. Similarly, impurities were removed, and purity of trans-1,3,3,3-tetrafluoropropene (1234zeE) was increased.

TABLE 2

|  | $CF_3-C \equiv CH$ | 1234zeE | 1243zf | 245fa | 1234zeZ | 1233zdE | Others |
|---|---|---|---|---|---|---|---|
| Before test (crude 1234zeE) | 0.0008 | 99.8674 | 0.0011 | 0.0665 | 0.0642 | 0.0000 | 0.0011 |
| Ex. 1 Zeolite 1 CaA | 0.0004 | 99.8712 | 0.0004 | 0.0650 | 0.0634 | 0.0000 | 0.0000 |
| Ex. 2 Zeolite 2 NaX | 0.0013 | 99.9924 | 0.0000 | 0.0017 | 0.0046 | 0.0000 | 0.0000 |
| Ex. 3 Zeolite 3 LiX | 0.0005 | 99.9770 | 0.0000 | 0.0066 | 0.0146 | 0.0000 | 0.0013 |
| Ex. 4 Zeolite 4 CaX | 0.0000 | 99.8984 | 0.0000 | 0.0227 | 0.0784 | 0.0000 | 0.0005 |

1234zeE (trans-$CF_3CH \equiv CH$), 1243zf ($CF_3CH \equiv CH_2$), 245fa ($CF_3CH_2CHF_2$), 1234zeZ (cis-$CF_3CH \equiv CH$), 1233zdE (trans-$CF_3CH \equiv CHCl$)

Example 5

There was conducted an adsorptive removal of impurities in the crude 1234zeE by the same procedure as that of Example 1, except in that 5 g of Zeolite 2 (NaX) and the crude 1234zeE having a composition shown in Table 2 were used. The results are shown in Table 3. Similarly, impurities were removed, and purity of trans-1,3,3,3-tetrafluoropropene (1234zeE) was increased.

TABLE 3

|  | 1234zeE | 1243zf | 1234zc | 245fa | 1234zeZ | 1233zdE | 1233zdZ | 142 | Others |
|---|---|---|---|---|---|---|---|---|---|
| Before test (crude 1234E) | 97.5374 | 0.0011 | 0.4460 | 0.0096 | 1.9779 | 0.0119 | 0.0010 | 0.0012 | 0.0139 |
| After test | 99.9026 | 0.0000 | 0.0415 | 0.0004 | 0.0412 | 0.0011 | 0.0000 | 0.0004 | 0.0128 |

1234zeE (trans-$CF_3CH=CH$), 1243zf ($CF_3CH=CH_2$), 1234zc ($CHF_2CH=CF_2$), 245fa ($CF_3CH_2CHF_2$), 1234zeZ (cis-$CF_3CH=CH$), 1233zdE (trans-$CF_3CH=CHCl$), 1233zdZ (cis-$CF_3CH=CHCl$), 142 ($C_2H_3ClF_2$)

Example 6

There was conducted an adsorptive removal of impurities in the crude 1234zeE by the same procedure as that of Example 1, except in that 5 g of Zeolite 2 (NaX) and the crude 1234zeE having a composition shown in Table 3 were used. The results are shown in Table 3. Purity of trans-1,3,3,3-tetrafluoropropene (1234zeE) was increased.

TABLE 4

|  | 1234zeE | 1243zf | 245fa | 1234zc | 1234zeZ | 1233zdE | Others |
|---|---|---|---|---|---|---|---|
| Before test (crude 1234Z) | 0.0089 | 0.0014 | 0.1408 | 0.0011 | 99.5866 | 0.0105 | 0.2507 |
| After test | 0.0090 | 0.0004 | 0.0575 | 0.0003 | 99.6937 | 0.0115 | 0.2276 |

1234zeE (trans-$CF_3CH=CH$), 1243zf ($CF_3CH=CH_2$), 245fa ($CF_3CH_2CHF_2$), 1234zc ($CHF_2CH=CF_2$), 1234zeZ (cis-$CF_3CH=CH$), 1233zdE (trans-$CF_3CH=CHCl$),

Example 7

A stainless steel tube having an inner diameter of 10 mm φ and a length of 400 mm was packed with 15 g of Zeolite 6. Filters having a pore size of 230 μm and made by U.S. Swagelok Company were installed on both ends, and it was vertically placed. The packing height of Zeolite 6 used for packing in the tube is 325 mm. As shown in Table 4, the crude 1234zez in the form of gas was supplied to the bottom of the tube at a rate of 5 cc/minute and allowed to flow. The results obtained by analyzing 42 hours later a gas discharged from an exit at the top by gas chromatography are shown in Table 4. There was no generation of 1233zd, and trans-1,3,3,3-tetrafluoropropene (1234zeE) having a high purity of 99.99% or higher was obtained.

Example 8

The same experiment as that of Example 7 was conducted, except using the above-mentioned Zeolite 7. The results obtained by analyzing in the same manner 42 hours later are shown in Table 4. There was no generation of 1233zd, and trans-1,3,3,3-tetrafluoropropene (1234zeE) having a high purity of 99.99% or higher was obtained.

EXPLANATION OF SIGNS

1: a tank packed with the crude 1234zeE

2: a line

3: An adsorption column packed with the solid adsorbent

4: a liquid delivery pump

The invention claimed is:

1. A method for purifying a trans-1,3,3,3-tetrafluoropropene, comprising the steps of:
   (a) dechlorinating a molecular sieve 13X to prepare a dechlorinated molecular sieve 13X; and
   (b) bringing a composition containing trans-1,3,3,3-tetrafluoropropene and at least one impurity selected from the group consisting of $C_2H_3ClF_2$, $CF_3CH_2CHClF$, $CF_3CH_2CHF_2$, $CHF_2CH=CF_2$, $CF_3CH=CHCl$, $CF_3CH=CH_2$, $CF_3C\equiv CH$, and cis-1,3,3,3-tetrafluoropropene into contact with the dechlorinated molecular sieve 13X as a solid adsorbent to reduce an impurity content thereof.

2. The purification method according to claim 1, wherein at least one impurity is selected from the group consisting of cis-1,3,3,3-tetrafluoropropene and $CF_3CH_2CHF_2$.

3. A solid-liquid, heterogeneous mixture, comprising:
   (a) a composition containing trans-1,3,3,3-tetrafluoropropene and at least one organic matter selected from the group consisting of $C_2H_3ClF_2$, $CF_3CH_2CHClF$, $CF_3CH_2CHF_2$, $CHF_2CH=CF_2$, $CF_3CH=CHCl$, $CF_3CH=CH_2$, $CF_3C\equiv CH$, and cis-1,3,3,3-tetrafluoropropene, and
   (b) a dechlorinated molecular sieve 13X as a solid adsorbent.

TABLE 5

|  |  | $CF_3-C\equiv CH$ | 1234zeE | 1243zf | 245fa | 1234zeZ | 1233zdE | Others |
|---|---|---|---|---|---|---|---|---|
|  | Before test (crude 1233E) | 0.0008 | 99.8674 | 0.0011 | 0.0665 | 0.0642 | 0.0000 | 0.0011 |
| Ex. 7 | Zeolite 6 (NaF aq. solution treatment) | 0.0007 | 99.9986 | 0.0000 | 0.0000 | 0.0007 | 0.0000 | 0.0000 |
| Ex. 8 | Zeolite 7 (pure water treatment) | 0.0008 | 99.9989 | 0.0000 | 0.0000 | 0.0003 | 0.0000 | 0.0000 |

1234zeE (trans-$CF_3CH=CH$), 1243zf ($CF_3CH=CH_2$), 245fa ($CF_3CH_2CHF_2$), 1233zc ($CHF_2CH=CF_2$), 1234zeZ (cis-$CF_3CH=CH$), 1233zdE (trans-$CF_3CH=CHCl$)

4. The purification method according to claim 1, wherein the dechlorination is conducted by immersing the molecular sieve 13X in an ion-exchanged water containing no chlorine ions or pure water.

5. The purification method according to claim 1, wherein the dechlorination is conducted by immersing the molecular sieve 13X in an alkali metal fluoride aqueous solution and then washing the molecular sieve 13X with an ion-exchanged water.

6. The purification method according to claim 5, wherein the alkali metal fluoride aqueous solution has a concentration of from 0.1 mass % to 5 mass % of an alkali metal fluoride.

7. The purification method according to claim 6, wherein the alkali metal fluoride is selected from the group consisting of KF, NaF, and CsF.

8. The purification method according to claim 7, wherein the alkali metal fluoride is NaF.

9. The purification method according to claim 1, further comprising the step of drying the dechlorinated molecular sieve 13X by heating.

* * * * *